(12) United States Patent
Quan et al.

(10) Patent No.: US 11,534,588 B2
(45) Date of Patent: Dec. 27, 2022

(54) FOAM SUPPORT SHEET FOR MICRONEEDLE ARRAY

(71) Applicant: COSMED PHARMACEUTICAL CO., LTD., Kyoto (JP)

(72) Inventors: Ying-Shu Quan, Kyoto (JP); Hiroshi Tanaka, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 352 days.

(21) Appl. No.: 16/630,398

(22) PCT Filed: Jul. 18, 2018

(86) PCT No.: PCT/JP2018/026854
§ 371 (c)(1),
(2) Date: Jan. 10, 2020

(87) PCT Pub. No.: WO2019/017369
PCT Pub. Date: Jan. 24, 2019

(65) Prior Publication Data
US 2021/0146104 A1    May 20, 2021

(30) Foreign Application Priority Data
Jul. 18, 2017  (JP) ............................. JP2017-139526

(51) Int. Cl.
*A61M 37/00*    (2006.01)
(52) U.S. Cl.
CPC ..... *A61M 37/0015* (2013.01); *A61M 2209/08* (2013.01)
(58) Field of Classification Search
CPC .......... A61M 37/0015; A61M 2209/08; A61M 2037/0023; A61L 31/048; A61L 31/06; A61L 31/146
See application file for complete search history.

(56) References Cited

U.S. PATENT DOCUMENTS

2003/0135161 A1* 7/2003 Fleming ............. A61B 5/14514
606/186
2014/0339117 A1 11/2014 Quan et al.
(Continued)

FOREIGN PATENT DOCUMENTS

DE  10 2008 057 822 A1   5/2010
JP    56-138081 U      10/1981
(Continued)

OTHER PUBLICATIONS

Notification of Reasons for Refusal for the Application No. 2017-139526 from Japan Patent Office dated Apr. 20, 2021.
(Continued)

*Primary Examiner* — Amber R Stiles
(74) *Attorney, Agent, or Firm* — Cheng Law Group, PLLC

(57) ABSTRACT

To provide a means which makes it possible to hold a microneedle array without an adhesive sheet and protect tips of microneedles.

A foam support sheet for a microneedle array, which has an open cell surface on at least one side, the open cell surface being an arrangement portion for the microneedle array holding the microneedle array with a microneedle side of the microneedle array facing downward; as well as a microneedle array sheet consisting of a microneedle array and a foam support sheet, the foam support sheet having an open cell surface on at least one side, and the microneedle array being arranged on the open cell surface with a microneedle side of the microneedle array facing downward.

6 Claims, 1 Drawing Sheet

(56) References Cited

U.S. PATENT DOCUMENTS

| | | |
|---|---|---|
| 2015/0335870 A1 | 11/2015 | Quan et al. |
| 2016/0206864 A1 | 7/2016 | Matonick et al. |
| 2017/0217656 A1 | 8/2017 | Yamada |

FOREIGN PATENT DOCUMENTS

| | | |
|---|---|---|
| JP | 62-59032 U | 4/1987 |
| JP | 63-120878 U | 8/1988 |
| JP | 2003-238347 A | 8/2003 |
| JP | 2009-273872 A | 11/2009 |
| JP | 2010-29634 A | 2/2010 |
| JP | 2012-213586 A | 11/2012 |
| JP | 2014-28108 A | 2/2014 |
| JP | 2014-79622 A | 5/2014 |
| JP | 2015-61677 A | 4/2015 |
| JP | 2015-181895 A | 10/2015 |
| JP | 2016-67618 A | 5/2016 |

OTHER PUBLICATIONS

English Translation of Written Opinion of the International Searching Authority (PCT/ISA/237) for Application No. PCT/JP2018/026854 dated Aug. 28, 2018 (English Translation mailed Jan. 30, 2020).

Cosmed Pharmaceutical Co., Ltd. "A4-4 Exhibits: Hyaluronate Microneedle, Melting Essence mask, Oil Gel Sheet, Ultra-thin stains and pimples care patch" at Exhibition CITE Japan 2017, The 8$^{th}$ Cosmetic Ingredients & Technology Exhibition Japan in Pacifico Yokohama on May 31, 2017,.

Cosmed Pharmaceutical Co., Ltd. product presentation: Presentation of a new hair growth tonic product using "microneedles", *"fa:sa" The first hair growth tonic in the world with a new concept which uses soluble microneedles!*handouts distributed to the media and in presentation on Jun. 6, 2017 at Tokyo Midtown Conference Room 7.

Cosmed Pharmaceutical Co., Ltd. "fa:sa" The Penetration Revolution Presentation Posting via Website: http://fa-sa.jp/ on Jun. 6, 2017.

International Search Report for the Application No. PCT/JP2018/026854 dated Aug. 28, 2018.

Written Opinion of the International Searching Authority (PCT/ISA/237) for Application No. PCT/JP2018/026854 dated Aug. 28, 2018.

* cited by examiner

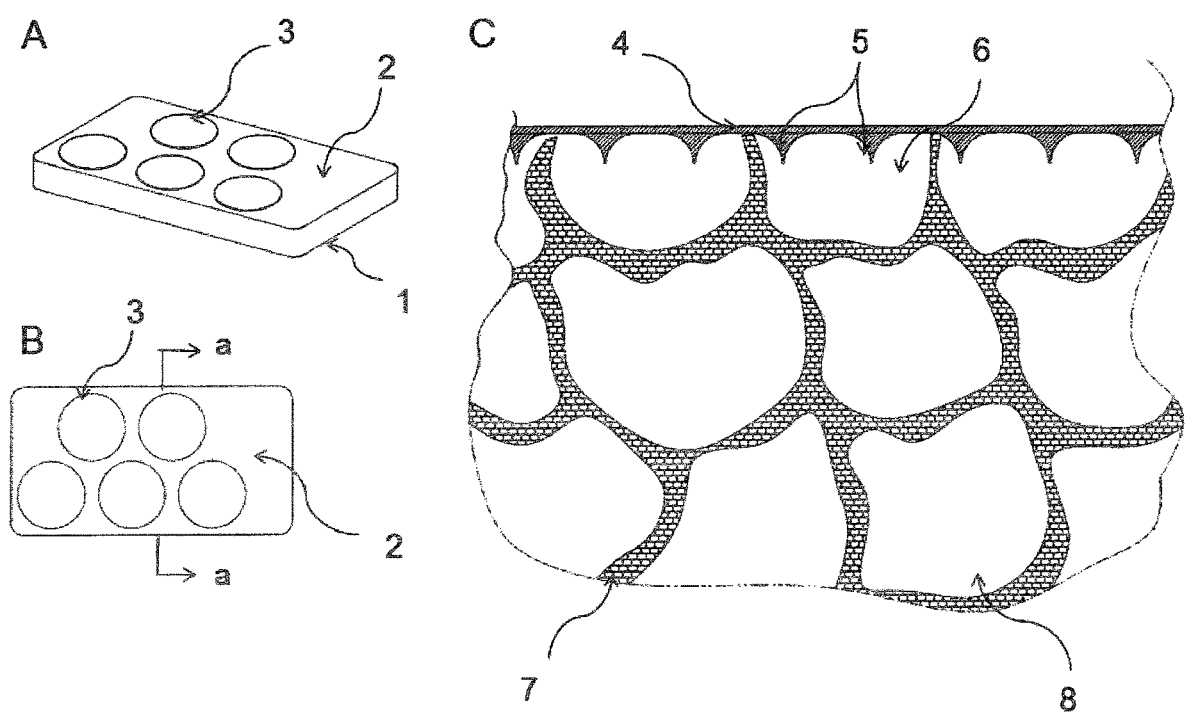

FOAM SUPPORT SHEET FOR MICRONEEDLE ARRAY

TECHNICAL FIELD

The present invention relates to a technique for protecting a microneedle array without an adhesive sheet or a technique for holding it during transportation.

BACKGROUND ART

Microneedle arrays refer to sheets on which numerous microneedles stand on a flexible substrate. The sheets have various shapes such as a circle, an oval, a comma shape, and a rectangle, and have areas of about 1 to 40 $cm^2$. These microneedle sheets have microneedles on one side. Since tip portions of the microneedles are extremely sharp, the tip portions are extremely weak against mechanical stimulation. Thus, it is necessary to exercise ingenuity so as not to damage the tip portions in storing or transporting the microneedle arrays.

For that purpose, the following methods have been adopted up to now. For example, a protective release sheet has been developed (Patent Document 1). The protective release sheet has a substrate which is a part of a flexible microneedle patch and also serves as a portion for holding a microneedle array during application or container storage. The substrate has one or more holes on the inside and one or more cutting lines running from the outer edge to the holes and holds a plurality of microneedle patches inside the holes. The protective release sheet is attached to an adhesive surface on a back surface of the microneedle array, and the microneedle array is brought into close contact with skin by applying the adhesive surface to a skin while peeling off the protective release sheet. In addition, a storage container has been developed which is dedicated to storing and transporting a microneedle patch held by a protective release sheet (Patent Documents 2 and 3). In addition, there is a storage container which can store a microneedle patch while holding an adhesive sheet portion of the microneedle patch by a trestle unit (Patent Document 4). Furthermore, a packaging body for a microneedle sheet has been developed, in which a plurality of microneedles of the microneedle sheet are formed by a plurality of micro-recesses on a sheet member and are also subsequently protected by the plurality of micro-recesses (Patent Document 5).

PRIOR ART DOCUMENTS

Patent Documents

Patent Document 1: Japanese Patent Application Laid-Open No. 2014-028108
Patent Document 2: Japanese Patent Application Laid-Open No. 2012-213586
Patent Document 3: Japanese Patent Application Laid-Open No. 2014-079622
Patent Document 4: Japanese Patent Application Laid-Open No. 2015-061677
Patent Document 5: Japanese Patent Application Laid-Open No. 2016-067618

SUMMARY OF INVENTION

Problem to be Solved

In all existing methods, a back surface of a microneedle array was protected with an adhesive sheet, and the adhesive sheet was held on a protective release sheet or the like, or otherwise, the microneedle array was held by bonding an adhesive surface of the adhesive sheet to a container without a protective release sheet. However, in these cases, the microneedles were administered to a human inevitably in such a manner that the microneedle array were integrally combined with the adhesive sheet. In a case of a microneedle array made of a resin capable of dissolving or swelling in a living body, if the microneedle array alone can be easily administered to a human skin without an adhesive sheet, and effects are advantageously exerted because water can be supplied to the microneedle array from the backside so as to remarkably accelerate intracellular dissolution of the microneedles. A problem of the present invention is to provide a means which makes it possible to hold a microneedle array without an adhesive sheet and protect tips of microneedles.

Solution to Problem

As a result of continuous and keen study under such a circumstance, the present inventors succeeded in protecting tip portions of microneedles by: processing a foam body such as an expanded plastic into a sheet; and holding a microneedle array on an upper surface of the sheet with a needle side of the microneedle array facing downward, leading to completion of the present invention.

The present invention is as follows.

[1] A foam support sheet for a microneedle array, which has an open cell surface on at least one side, the open cell surface being an arrangement portion for the microneedle array holding the microneedle array with a microneedle side of the microneedle array facing downward.
[2] The foam support sheet according to [1], in which open cells on the open cell surface are portions for holding the microneedles.
[3] The foam support sheet according to [1] or [2], made of a synthetic polymer material.
[4] The foam support sheet according to [3], in which the synthetic polymer material is made of polyurethane, polystyrene, polyolefin, phenol resin, polyvinyl chloride, urea resin, or a mixture thereof.
[5] The foam support sheet according to any one of [1] to [4], which has an expansion ratio of 5 or higher.
[6] The foam support sheet according to [5], in which the expansion ratio is 10 or higher.
[7] A microneedle array sheet consisting of a microneedle array and a foam support sheet, the foam support sheet having an open cell surface on at least one side, and the microneedle array being arranged on the open cell surface with a microneedle side of the microneedle array facing downward.
[8] The microneedle array sheet according to [7], in which the microneedle array includes a water-soluble polymer or a water-swellable resin as a base.
[9] The microneedle array sheet according to [7] or [8], in which open cells on the open cell surface hold tip portions of the microneedles.
[10] The microneedle array sheet according to any one of [7] to [9], in which the foam support sheet is made of a synthetic polymer material.
[11] The microneedle array sheet according to [10], in which the synthetic polymer material is made of polyurethane, polystyrene, polyolefin, phenol resin, polyvinyl chloride, urea resin, or a mixture thereof.

[12] The microneedle array sheet according to any one of [7] to [11], in which the foam support sheet has an expansion ratio of 5 or higher.

[13] The microneedle array sheet according to [12], in which the expansion ratio is 10 or higher.

Effects of Invention

Since tip portions of microneedles are extremely sharp, the tip portions are weak against mechanical stimulation. Therefore, it is necessary to variously exercise ingenuity so as not to bring the tip portions of the microneedles into contact with a holding sheet or a storage container. However, in the present invention, the foam body sheet holds the microneedle array. The microneedle array can be held on the foam body sheet by intentionally bringing the foam body sheet having an expanded (foam) or meshed surface into contact with the tip portions of the microneedles. Furthermore, the tip portions of the microneedles in contact with the foam body sheet are accommodated in voids of the foam body sheet and unexpectedly protected with no damage.

BRIEF DESCRIPTION OF DRAWINGS

FIG. 1 illustrates an aspect of a microneedle array sheet. FIG. 1A is a perspective view, FIG. 1B is a plan view, and FIG. 1C is a partially-enlarged sectional view. In FIG. 1C, a needle interval of microneedles 5 is 600 μm.

DESCRIPTION OF EMBODIMENTS

Foam Support Sheet

The foam support sheet according to the present invention refers to a foam body sheet having an open cell surface on at least one side and supporting a microneedle array. The open cell surface refers to a surface in which cells formed on a surface of a foam body are opened and form a mesh shape as a whole. The open cell surface may be formed on only one side or on both sides.

In the present invention, any resin foam body can be used to form a foam support sheet. The resin foam body of a closed-cell type or a continuous-cell type may be used, although the continuous cell type is preferable because of open cells connecting and communicating with each other. A resin foam body of a closed-cell-type or having a surface without open cells may be formed into a foam support sheet by slicing the surface so as to open cells on at least one side.

The open cell surface is an arrangement portion for holding the microneedle array with a microneedle side of the microneedle array facing downward (with the substrate side of the microneedle array facing upward).

In the foam support sheet according to the present invention, the microneedle array is arranged on the open cell surface with the microneedle side facing downward so that each open cell serves as a holding portion for holding the tip portion of the microneedle. That is, the open cells in the foam support sheet according to the present invention have functions of locking the tip portions of the sharp microneedles for holding the whole microneedle array, and of protecting the tip portions having a low mechanical strength. A locking position can be arbitrarily set as long as the whole microneedle array is positioned within the open cell surface.

A raw material for the foam support sheet may be, but is not particularly limited to, a synthetic resin. Examples of the synthetic resin include polyurethane, polystyrene, polyolefins (such as polyethylene and polypropylene), phenol resin, polyvinyl chloride, urea resin, and the like.

A shape and a size of the foam support sheet can be arbitrarily set depending on a shape and a number of microneedle arrays to be arranged on the sheet. When arranging a plurality of microneedle arrays, it is preferable to provide a margin for avoiding overlapping of the arrays. A thickness of the foam support sheet is not particularly limited as long as it can hold the microneedle array and protect the microneedles. The thickness is generally about 0.3 to 50 mm, preferably 1 to 30 mm.

Examples of a method for producing the foam support sheet include a method in which a foam body produced by a known chemical expanding or physical expanding method is used as it is, or alternatively, a method in which a produced foam body block is shaped by slicing, slitting, punching, or the like. A foam body having continuous cells can be used as it is. However, a closed-cell-type foam body has a smooth surface and therefore cannot be used as it is and should be processed by slicing and the like so that an inner cell portion can be used as an outermost surface. Partition portions and space portions coexist on a plane of the outermost surface depending on the expansion ratio. On an outermost surface of a foam body having an expansion ratio of 50 or higher, partition portions account for about 2% of an area of an outermost part. The needle tip portions of the microneedles account for about 1% of an area of the microneedle array. Thus, the probability that the partition portions come into contact with the microneedles to damage the needles is extremely low.

The expansion ratio of the foam support sheet or the foam body as a base thereof needs to be 5 or higher, preferably 10 or higher. If the expansion ratio is lower than 5, a theoretical area ratio of the partition portions on the outermost part (microneedle array contact surface) is 25% or higher, and a probability of damaging the microneedles in contact with the partition portions increases. The upper limit of the expansion ratio is not particularly limited as long as the formed body can be produced as a molded article. The foam body is composed of cell portions and partition portions. A substrate portion of the microneedle array is held in contact with the partition portions and the tips of the needles are held in cell spaces. Therefore, a size of the cell portion is important. Assuming that the cell portion is a sphere, a diameter of the cell portion needs to be larger than the diameter of the microneedle tip. Specifically, the diameter needs to be larger than 50 μm, preferably larger than 20 μm. In addition, a thickness of the partition portion is preferably small. Specifically, the thickness is preferably 200 μm or less, more preferably 100 μm or less. Furthermore, when focusing on rigidity as a mechanical strength of the foam body, the foam body having lower expansion ratio and formed of the foam body material with higher rigidity would have higher rigidity. Support sheets were prepared using various foam bodies having different rigidities, microneedles were pressed against the support sheets so as to evaluate degrees of damage of the microneedles. As a result, it was found that a rigidity of 5.0 N or higher increased the degree of damage of the microneedles. Consequently, in the present invention, the rigidity is preferably 5.0 N or lower, and more preferably 3.0 N or lower. In the present invention, the rigidity is defined as a force required for compressing the foam body to 10% of the original thickness by pressing a 1 $cm^2$ flat plate against the plane of the foam body using a tensile-compression testing machine.

Microneedle Array Sheet

A microneedle array sheet according to the present invention is composed of a microneedle array and a foam support sheet. The foam support sheet has an open cell surface on at least one side, and the microneedle array is arranged on the open cell surface with the microneedle side facing downward.

The material for the microneedle array is not particularly limited and may be a non-biosoluble material such as a silicone resin and a metal, or a biosoluble or water-swellable material such as a water-soluble polymer and a water-swellable resin. Since the foam support sheet according to the present invention is suitable for holding the microneedle array having the flexible substrate, a microneedle array including a water-soluble polymer or a water-swellable resin as a base is preferable.

The water-soluble polymer or water-swellable resin used in the present invention may be any resin as long as it can dissolve or swell in a living body. Examples of the resin include: a polysaccharide such as glycogen, dextrin, dextran, dextran sulfate, sodium chondroitin sulfate, hydroxypropylcellulose, alginic acid, agarose, chitin, chitosan, pullulan, amylopectin, starch, hyaluronic acid, and carboxymethylcellulose; a protein such as collagen, gelatin, and albumin; and a synthetic polymer such as polyvinyl alcohol, carboxyvinyl polymer, sodium polyacrylate, polyvinylpyrrolidone, and polyethyleneglycol. Above all, a polymer substance selected from hyaluronic acid, starch, collagen, gelatin, polyvinylpyrrolidone, and polyethyleneglycol is preferable. These water-soluble polymers or water-swellable resins may be used alone or in combination of two or more.

Hyaluronic acid is a kind of glycosaminoglycan (mucopolysaccharide) and has a structure in which disaccharide units of N-acetylglucosamine and glucuronic acid are linked. Examples of the hyaluronic acid include: hyaluronic acid of biological origin isolated from cockscomb, umbilical cord, or the like; and a cultured hyaluronic acid mass-produced from *Lactobacillus, Streptococcus*, or the like. Collagen derived from the living body cannot be completely removed from hyaluronic acid of biological origin, and the remaining collagen may generate adverse effects. Therefore, the cultured hyaluronic acid containing no collagen is preferable. Consequently, it is preferable that 50% by weight or more of the hyaluronic acid is cultured hyaluronic acid.

When a microneedle array is manufactured using water-soluble polymer substances selected from hyaluronic acid, starch, collagen, gelatin, polyvinylpyrrolidone and polyethyleneglycol as components, decreasing its weight average molecular weight results in the microneedle array which is hard and easily pierces a skin but easily breaks during storage and skin piercing due to its decreased mechanical strength. On the contrary, increasing its weight average molecular weight results in the microneedle array which hardly breaks during storage and skin piercing due to its improved mechanical strength and tenacity but hardly pierces the skin due to its decreased hardness. Consequently, the weight average molecular weight is preferably 5,000 to 2,000,000.

The microneedle array may be formed from a mixture of a high-molecular-weight polymer substance having a weight average molecular weight of 100,000 or higher and a low-molecular-weight polymer substance having a weight average molecular weight of 50,000 or lower so that the microneedle array easily pierces the skin and hardly break in insertion into the skin as well as easily dissolve in the body. The weight average molecular weight of the high-molecular-weight polymer substance only needs to be 100,000 or higher, and preferably 2,000,000 or lower. In addition, the weight average molecular weight of the low-molecular-weight polymer substance only needs to be 50,000 or lower, and preferably 1,000 or higher. It should be noted that, in the present invention, the weight average molecular weight is a value measured by gel permeation chromatography (GPC).

A mixture ratio of the high-molecular-weight high polymer substance and the low-molecular-weight polymer substance varies depending on the type and the weight average molecular weight of each polymer substance. Thus, the mixture ratio may be appropriately determined so as to obtain a preferable mechanical strength and hardness, but in general, the mixture is preferably composed of 40 to 95% by weight of the high-molecular-weight polymer substance and 60 to 5% by weight of the low-molecular-weight polymer substance.

The microneedle array can be mass-produced using a mold (die). A microneedle array including an injection-moldable polymer as a base may be manufactured by injection-molding the base using a die (e.g. method described in Japanese Patent Application Laid-Open No. 2003-238347, paragraphs [0017] and [0018]). For the injection molding die, stainless steel, heat-resistant steel, superalloy, or the like can be used. A typical die has slits corresponding to 100 to 1000 microneedles per square centimeter for forming a microneedle shape. A length of the slit corresponds to a length of the microneedle and is normally 100 to 1000 μm. When using hyaluronic acid, dextran, polyvinylpyrrolidone, sodium chondroitin sulfate, hydroxypropylcellulose, polyvinyl alcohol, and a mixture thereof as a base, a base aqueous solution can be poured into a mold, dried and then released from the mold (e.g. method described in Japanese Patent Application Laid-Open No. 2009-273872, paragraphs [0029] to [0031]).

The microneedle array may contain or may be coated with various drugs.

The microneedle array produced as described above can have any shape depending on an application site. The typical shape is a circle, an oval, a comma shape, or the like. The microneedle array having these shapes is arranged on the open cell surface of the foam support sheet according to the present invention with the microneedle side facing downward so as to provide the microneedle array sheet according to the present invention. The form support sheet holds the tip portions of the sharp microneedles in the open cells and holds bottom surfaces of the microneedles on the open cell surface. Thus, the form support sheet holds the whole microneedle array while it protects the tip portions having low mechanical strength. The locking position can be arbitrarily set as long as the whole microneedle array is positioned within the open cell surface. Furthermore, on the microneedle array sheet according to the present invention, one or a plurality of microneedle arrays can be provided depending on the application.

An embodiment of the microneedle array sheet according to the present invention is illustrated in FIG. 1. Five circular microneedle arrays 3 are arranged on an open cell surface 2 of a foam support sheet 1 (FIG. 1A and FIG. 1B). In the enlarged sectional view of the microneedle array sheet (FIG. 1C), the microneedle array is arranged such that a substrate 4 faces upward, and microneedles 5 face downward and are held in open cells 6. In the inside of the foam support sheet, there is an expanded structure composed of partition portions 7 and cell portions 8.

Since an adhesive is not used for the microneedle array sheet according to the present invention, the microneedle array can be easily taken out from the foam support sheet.

After the microneedle patch is applied to a skin, adherence of the microneedle patch to the skin can be maintained by skin moisture or appropriate hydration. Alternatively, the microneedle array applied to the skin can be adhered by an adhesive tape or the like.

EXAMPLES

Hereinafter, the present invention will be explained with reference to examples. However, the present invention is not limited to the examples.

Example 1

"SAKURA BIHAKU" (registered trademark) microneedle array manufactured by CosMED Pharmaceutical Co. Ltd. was used as the microneedle array. This product included hyaluronic acid as a main ingredient and had a needle length of 200 μm, and a needle interval of 600 μm. The array of the product was a circle having a diameter of 15 mm and had about 600 needles. A thickness of a substrate of the array was about 40 μm. The needles were a stratovolcano shape, and a diameter of the needle tip portion was about 50 μm.

A sheet having a thickness of 7 mm, a width of 25 mm, and a length of 60 mm, obtained by slicing a heat-resistant expanded polyethylene foam (closed-cell-type foam body) manufactured by Fuji Gomu Co. Ltd. was used as the foam support sheet. The sheet had an expansion ratio of 70. Three microneedle arrays were settled on the sheet with a needle portion facing downward and sufficiently pressed by hand. Before and after the pressing, a state of the needle portion was microscopically observed. As a result, deformation of the needles due to the pressing was not observed.

Example 2

"SAKURA BIHAKU" (registered trademark) microneedle array manufactured by CosMED Pharmaceutical Co. Ltd. was used as the microneedle array. A sheet having a thickness of 7 mm, a width of 25 mm, and a length of 60 mm, obtained by slicing a soft urethane foam (continuous-cell-type foam body) manufactured by Fuji Gomu Co. Ltd. was used as the foam support sheet. The sheet had an expansion ratio of 5. Three microneedle arrays were settled on the sheet with a needle portion facing downward and sufficiently pressed by hand. Before and after the pressing, a state of the needle portion was microscopically observed. Deformation of the needles due to the pressing was not observed.

Example 3

"SAKURA BIHAKU" (registered trademark) microneedle array manufactured by CosMED Pharmaceutical Co. Ltd. was used as the microneedle array. A sheet having a thickness of 7 mm, a width of 25 mm, and a length of 60 mm, obtained by slicing an expanded polystyrene (closed-cell-type foam body) manufactured by Matsubara Industry Inc. was used as the foam support sheet. The sheet had an expansion ratio of 10. Three microneedle arrays were settled on the sheet with a needle portion facing downward and sufficiently pressed by hand. Before and after the pressing, a state of the needle portion was microscopically observed. As a result, 25 needles were deformed by the pressing which accounted for 5% or lower of the total.

Comparative Example 1

The expanded polystyrene used in Example was cut and dissolved in an extra-pure reagent acetone (NACALAI TESQUE, INC.) to obtain about 5% polystyrene solution. This solution was allowed to stand for a whole day and night for volatilizing acetone, to obtain a semisolid acetone-polystyrene mixture. This mixture was cut into 10×10×10 mm blocks, the blocks were put into boiling water and heated for 5 minutes to expand the blocks. The blocks were taken out, and dried at 40° C. for 48 hours. As a result of measuring sizes and weights of the blocks, an expansion ratio was 4.5. The block was cut into a sheet having a thickness of 7 mm, a width of 20 mm, and a length of 20 mm. Three "SAKURA BIHAKU" (registered trademark) microneedle array were settled on the sheet with the needle portion facing downward and sufficiently pressed by hand. Before and after the pressing, a state of the needle portion was microscopically observed. As a result, 145 needles were deformed by the pressing which accounted for 24% of the total, indicating that the sheet was unsuitable as a microneedle support sheet. We think that this is because the foam body having the expansion ratio of 4.5 had a thick partition so that the probability that the microneedles came into contact with the partition portions was increased when the microneedles were settled on the open cell surface.

REFERENCE NUMERALS

1 Foam support sheet
2 Arrangement portion (open cell surface)
3 Microneedle array
4 Substrate of microneedle array
5 Microneedle
6 Open cell
7 Partition portion
8 Cell portion

The invention claimed is:

1. A microneedle array sheet consisting of a microneedle array and a foam support sheet, wherein
    the foam support sheet has an open cell surface on at least one side,
    the microneedle array is arranged on the open cell surface with a microneedle side of the microneedle array facing downward into the foam support sheet, and
    the microneedle array includes a water-soluble polymer or a water-swellable resin as a base.

2. The microneedle array sheet according to claim 1, wherein open cells on the open cell surface hold tip portions of microneedles.

3. The microneedle array sheet according to claim 1, wherein the foam support sheet is made of a synthetic polymer material.

4. The microneedle array sheet according to claim 3, wherein the synthetic polymer material is made of polyurethane, polystyrene, polyolefin, phenol resin, polyvinyl chloride, urea resin, or a mixture thereof.

5. The microneedle array sheet according to claim 1, wherein the foam support sheet has an expansion ratio of 5 or higher.

6. The microneedle array sheet according to claim 5, wherein the expansion ratio is 10 or higher.

* * * * *